(12) United States Patent
Wu et al.

(10) Patent No.: US 11,596,177 B2
(45) Date of Patent: Mar. 7, 2023

(54) HEATING DEVICE AND SMOKING SET HAVING SAME

(71) Applicant: Shenzhen First Union Technology Co., Ltd., Shenzhen (CN)

(72) Inventors: Zexin Wu, Shenzhen (CN); Yonghai Li, Shenzhen (CN); Zhongli Xu, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 1042 days.

(21) Appl. No.: 16/262,936

(22) Filed: Jan. 31, 2019

(65) Prior Publication Data
US 2019/0230987 A1    Aug. 1, 2019

(30) Foreign Application Priority Data
Jan. 31, 2018 (CN) .......................... 201820171493.9

(51) Int. Cl.
*A24F 40/465* (2020.01)
*H05B 6/10* (2006.01)
(Continued)

(52) U.S. Cl.
CPC ............ *A24F 40/465* (2020.01); *A24F 40/51* (2020.01); *A24F 40/57* (2020.01); *H05B 3/26* (2013.01); *H05B 3/42* (2013.01); *H05B 6/10* (2013.01); *H05B 6/105* (2013.01); *H05B 6/36* (2013.01); *A24F 40/20* (2020.01); *A61M 15/06* (2013.01); *H05B 6/04* (2013.01); *H05B 6/108* (2013.01)

(58) Field of Classification Search
CPC ........ A24F 40/465; A24F 40/51; A24F 40/57; A24F 40/20; H05B 3/26; H05B 3/42; H05B 6/10; H05B 6/105; H05B 6/36; H05B 6/108; H05B 6/04; A61M 15/06
See application file for complete search history.

(56) References Cited

U.S. PATENT DOCUMENTS 585,310 A * 6/1897 Fraley ................... H05B 6/105
    336/107
9,516,899 B2 * 12/2016 Plojoux ................... A24F 40/50

FOREIGN PATENT DOCUMENTS

| CN | 107 454 700 A | 12/2017 |
| WO | 2013/098395 A1 | 7/2013 |
| WO | 2017/072149 A1 | 5/2017 |

* cited by examiner

*Primary Examiner* — Abdullah A Riyami
*Assistant Examiner* — Justin M Kratt
(74) *Attorney, Agent, or Firm* — PROI Intellectual Property US; Klaus Michael Schmid

(57) ABSTRACT

A heating device includes a base; a supporter disposed on the base, the supporter has a chamber therein and the chamber being configured for receiving the tobacco cigarette; an electromagnetic induction coil, wound around the supporter and configured for generating an alternative magnetic field in the chamber; at least one first heating element disposed in the chamber; when the tobacco cigarette is disposed in the chamber, the at least one first heating element contacts an outer surface of the tobacco cigarette and is configured for generating a vortex in the alternative magnetic field to heat the tobacco cigarette; and a second heating element disposed on the base; when the tobacco cigarette is disposed in the chamber, the second heating element is inserted into the tobacco cigarette and configured to generate a vortex in the alternative magnetic field to heat the tobacco cigarette.

16 Claims, 6 Drawing Sheets

(51) Int. Cl.
*A24F 40/51* (2020.01)
*A24F 40/57* (2020.01)
*H05B 3/26* (2006.01)
*H05B 3/42* (2006.01)
*H05B 6/36* (2006.01)
*A24F 40/20* (2020.01)
*H05B 6/04* (2006.01)
*A61M 15/06* (2006.01)

HEATING DEVICE AND SMOKING SET HAVING SAME

TECHNICAL FIELD

The present disclosure relates to the field of smoking sets, and particularly to a heating device and a smoking set having same.

BACKGROUND ART

The tobacco cigarette as an additive is adored by lots of people. However, tars and carbon monoxide etc. are harmful to people's health. Especially, tens of substances in the tar are carcinogens, which immensely affect people's health. Currently, many countries are gradually prohibiting smoking tobacco cigarettes in the public. However, for the heavy smokers, it is difficult for them not to smoke, which is a painful thing. Therefore, many alternatives appeared in the market such as, repatons and electronic cigarettes etc.

The electronic cigarette heats the tobacco cigarette or cartridge for atomization, so as to generate an aerosol. Since the electronic cigarette has similar flavor and appearance with the real tobacco cigarette, ridding the harmful substances such as tars and particulate matters in the tobacco cigarette, the electronic cigarette become more and more popular among the users.

In prior art, two ways are adopted to heat the tobacco cigarette: 1, inserting a heating element into the tobacco cigarette, the heating element generates heat by means of electromagnetic induction to heat the tobacco cigarette; 2, by integrating central heating and around heating, by means of the electromagnetic induction, the heating element generates heat for heating the tobacco cigarette.

During invention process, a method known to the inventors: the central heating as described supra would cause heating unevenly, that is, inside the tobacco cigarette has high temperature whereas outside the tobacco cigarette has low temperature, which tremendously affect taste of the electronic cigarette; however, the around heating as described supra generally generates a closed annulus, but the annulus-shaped metallic heating element would concentrate the electromagnetic inductive lines on the closed annulus itself, which may cause magnetic shielding to the tobacco cigarette disposed at a central of the closed annulus, so that the tobacco cigarette absorbing and transforming the magnetic flux would be affected, with consequently low heating efficiency and uneven heating to the tobacco cigarette to damage taste of the electronic cigarette.

SUMMARY

In view of the drawbacks in the prior art, the present disclosure relates to a heating device and a smoking set having the same, which are capable of improving efficiency of central heating with evenly heating, such that the electronic cigarette has a good taste.

In order to solve the above technical problem, the present disclosure provides a heating device for heating tobacco cigarette according to independent claim 1 whereas various embodiments of the heating device and improvements thereto are recited in the dependent claims. The heating device includes a base; a supporter disposed on the base, the supporter has a chamber therein; the chamber being configured for receiving the tobacco cigarette; an electromagnetic induction coil, wound around the supporter and configured for generating an alternative magnetic field in the chamber; at least one first heating element, disposed in the chamber, when the tobacco cigarette is disposed in the chamber, the at least one first heating element contacts an outer surface of the tobacco cigarette and configured for generating a vortex in the alternative magnetic field to heat the tobacco cigarette; and a second heating element disposed on the base, when the tobacco cigarette is disposed in the chamber, the second heating element is inserted into the tobacco cigarette and configured to generate a vortex in the alternative magnetic field to heat the tobacco cigarette;

the at least one first heating element is disposed around a periphery of the second heating element, and the at least one first heating element forms a cut extending along an axial direction of the electromagnetic induction coil.

In some embodiments, the at least one first heating element includes two first heating elements, and the two first heating elements are spaced from each other by a predetermined distance along a circumferential direction of an inner wall of the chamber, thus forming the cut.

In some embodiments, the two first heating elements include a first arc-shaped heating piece and a second arc-shaped heating piece matched with the outer surface of the tobacco cigarette, and the first arc-shaped heating piece and the second arc-shaped heating piece are symmetrically disposed at two sides of the second heating element.

In some embodiments, the second heating element is a plate-shaped structure with a first surface and a second surface, the first surface has a larger area than the second surface, the first surface faces the cut.

In some embodiments, the first surface is perpendicular with a line connecting two ends of the first arc-shaped heating piece, and the first surface is perpendicular with a line connecting two ends of the second arc-shaped heating piece; the second surface is parallel with a line connecting two ends of the first arc-shaped heating piece, and the second surface is parallel with a line connecting two ends of the second arc-shaped heating piece.

In some embodiments, the heating device further includes a heat insulating layer, the heat insulating layer is disposed between the electromagnetic inductive coil and the at least one first heating element, the heat insulating layer is configured to reduce heat in the chamber transferring outside.

In some embodiments, the base includes a bulge part and a substrate, the bulge part is inserted into the chamber of the supporter to allow the supporter to be installed in the base.

In some embodiments, the base includes a fixing structure, configured to fix the second heating element in the base.

In some embodiments, the heating device further includes a temperature sensor, the temperature sensor is disposed on the second heating element or the at least one first heating element, or between the at least one first heating element and the second heating element.

To solve the above problem, the present disclosure further provides an electronic smoking set having the heating device as described supra and a power supply module; the power supply module is coupled with the electromagnetic inductive coil in the heating device and configured for supplying an alternating current to the electromagnetic inductive coil.

Additional aspects and advantages of the present disclosure will be: the present disclosure relates to a heating device and a smoking set having same; when the first heating element heats the tobacco cigarette from outside to inside, while the second heating element heats the tobacco cigarette from inside to outside, therefore heating the tobacco cigarette evenly. Moreover, since the first heating element has at least one cut extending along an axial direction of the electromagnetic inductive coil, the cut may ensure the second heating element to absorb sufficient electromagnetic flux, so as to improve the heating efficiency of the second heating element as well as improve the heating efficiency for heating the tobacco cigarette, therefore ensuring the tobacco cigarette to be heated evenly, making the taste of the tobacco cigarette consistent during smoking, improving the taste of the electronic smoking set and improving user experience.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

The structure and operating principle of the above heating element with temperature control and the low-temperature baked smoking set having same are illustrated below, mainly shown from FIG. 1 to FIG. 12 in further detail using exemplary embodiments.

Figure 1:
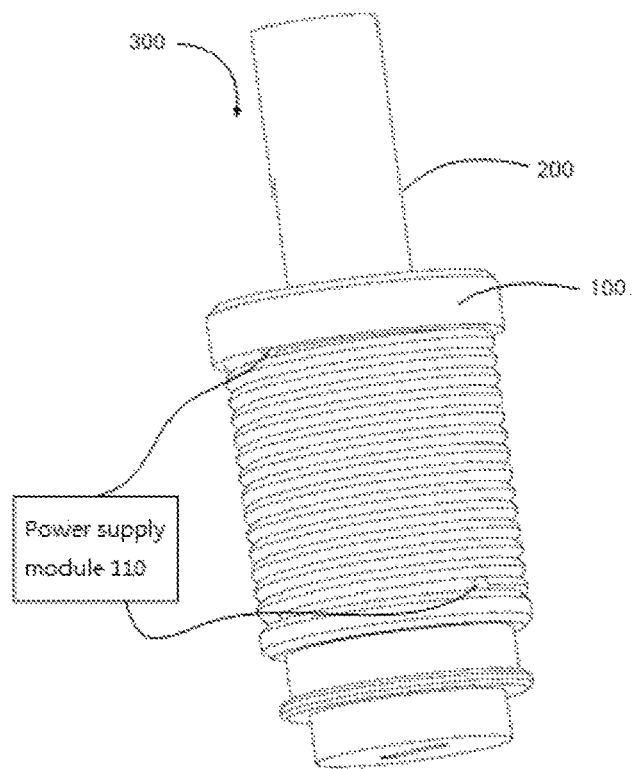
FIG. 1 is a cross-sectional view of an electronic smoking set in accordance with one embodiment of the present disclosure.
Figure 2:
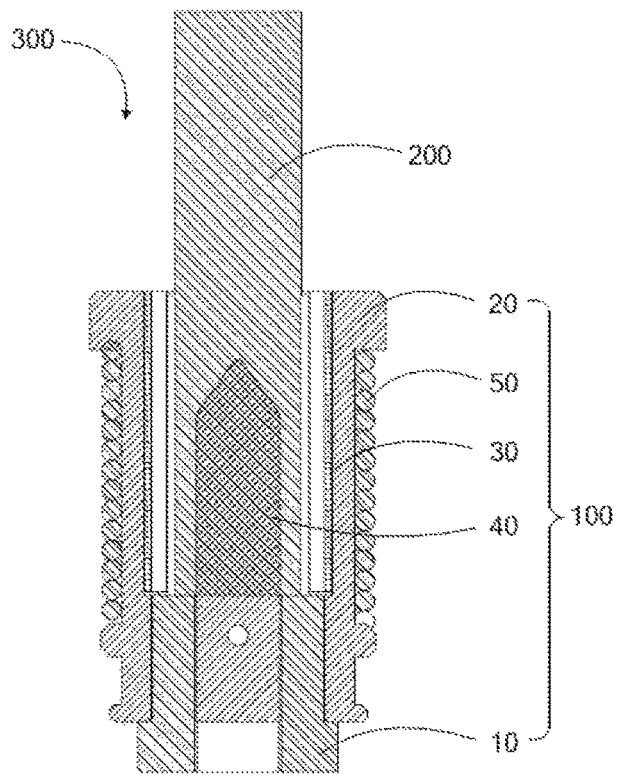
FIG. 2 is a cross-sectional view of the electronic smoking set without the power supply module in accordance with one embodiment of the present disclosure.
Figure 3:
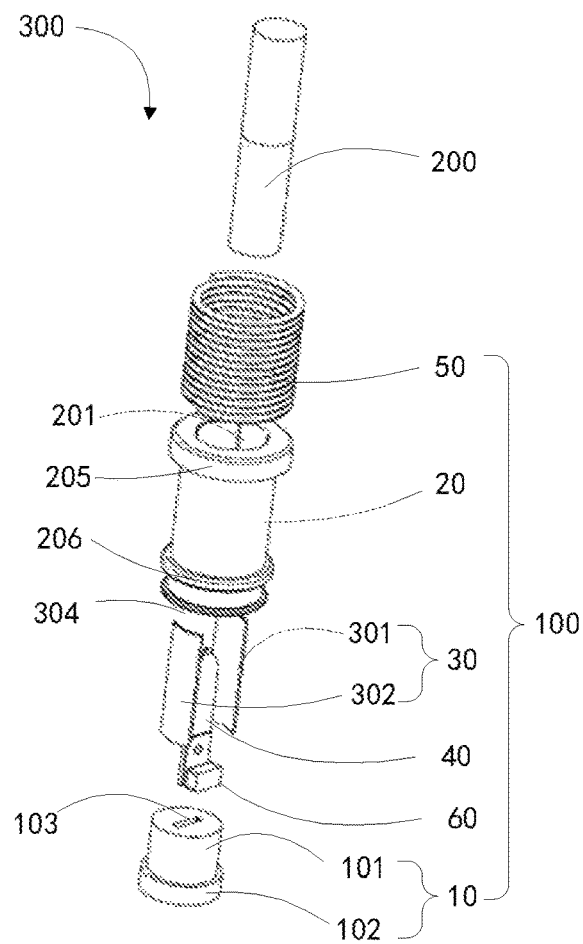
FIG. 3 is an exploded view of the electronic smoking set without the power supply module in accordance with one embodiment of the present disclosure.

Referring to FIGS. 1-3, which provide an electronic smoking set in accordance with embodiments of the present disclosure. The electronic smoking set 300 includes a heating device 100, a power supply module 110 and a tobacco cigarette 200. As used supra, the power supply module 110 is coupled with the electromagnetic inductive coil 50 in the heating device 100 and configured for supplying an alternating current to the electromagnetic inductive coil 50. The heating device 100 is configured to heat the tobacco cigarette 200. The tobacco cigarette 200 may be one or more tobacco shaped in rods. The tobacco cigarette 200 is disposed inside the heating device 100. More specifically, the heating device 100 has a chamber 201 therein configured for receiving the tobacco cigarette 200. The heating device 100 is configured to heat the tobacco cigarette 200, making the tobacco cigarette 200 to generate an aerosol drawn directly in combusting and non-burning methods, that is, the tobacco cigarette 200 doesn't need to be burnt to generate tar etc. some toxic gas, therefore decreasing the detrimental on the smokers' health.

The heating device 100 will be described in detail hereinafter in accordance with embodiments of the present disclosure.

Figure 4:
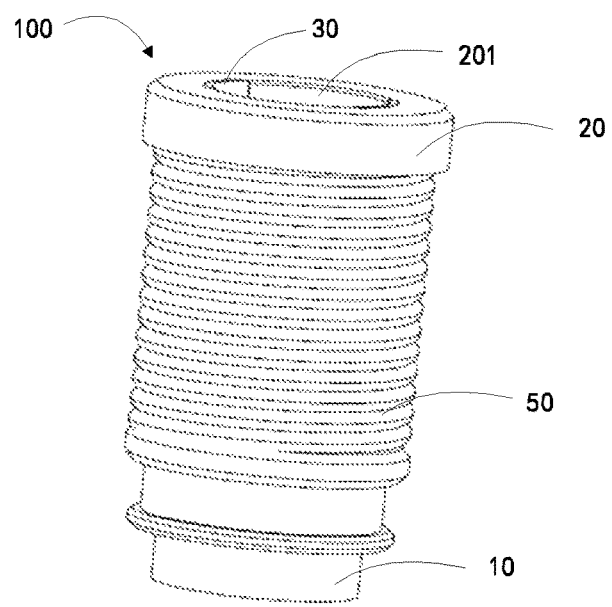
FIG. 4 illustrates the heating device in the electronic smoking set in FIG. 1.
Figure 5:
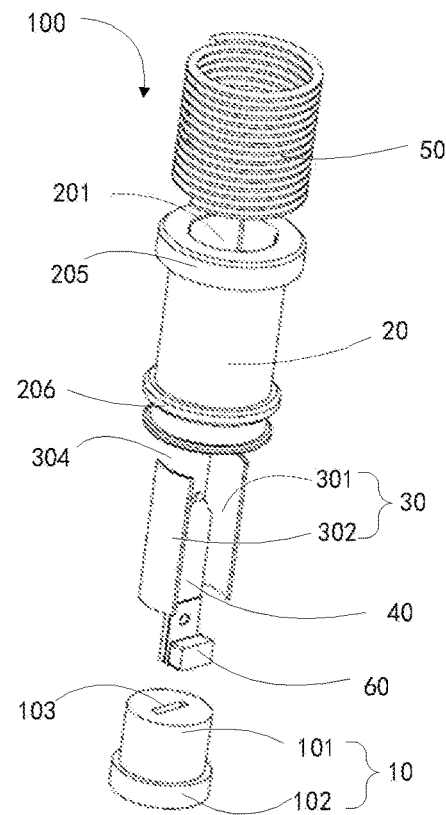
FIG. 5 is an exploded view of the heating device in the electronic smoking set in FIG. 1.
Figure 6:
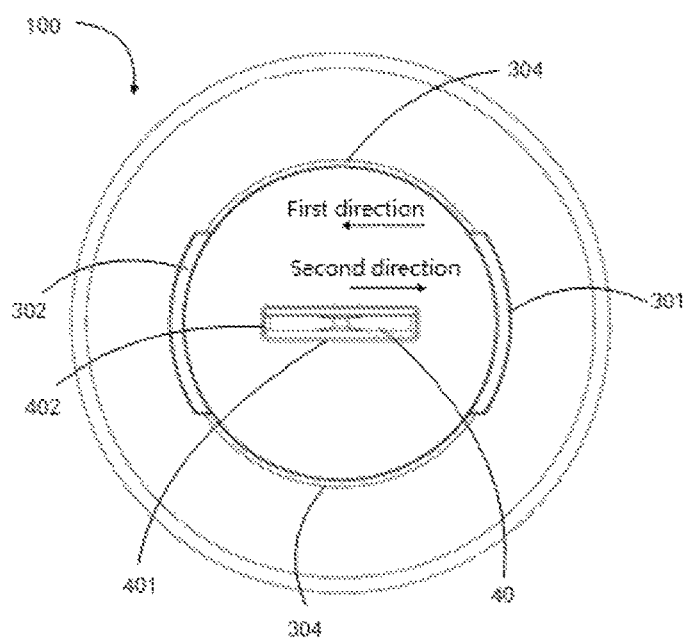
FIG. 6 is a top view of the heating device in the electronic smoking set in FIG. 1.

With reference to FIGS. 4 to 6, together with FIG. 2, the heating device 100 includes a base 10, a supporter 20, at least one first heating element 30, a second heating element 40 and an electromagnetic induction coil 50. As used herein, the supporter 20 is installed on the base 10. The supporter 20 has a chamber 201 therein configured for receiving the tobacco cigarette 200. The electromagnetic induction coil 50 is wound around the supporter 20 and configured for generating an alternative magnetic field in the chamber 201, such that the at least one first heating element 30 and second heating element 40 generate vortexes respectively. The at least one first heating element 30 is disposed in the chamber 201, when the tobacco cigarette 200 is received in the chamber 201, the at least one first heating element 30 contacts an outer surface of the tobacco cigarette 200 and generates a vortex in the alternative magnetic field to heat the tobacco cigarette 200, that means, heating outside the tobacco cigarette 200 directly. Moreover, the at least one first heating element 30 is disposed around a periphery of the second heating element 40 to form a cut 304 extending along an axial direction of the induction coil 50, which may ensure sufficient usage of the electromagnetic flux without influencing the second heating element 40 to absorb and transform the electromagnetic flux. The electromagnetic inductive lines in the chamber 201 passing through the chamber 201 are parallel with the axial direction of the induction coil 50. Along a circumferential direction of the chamber 201, where the cut 304 is located the electromagnetic inductive lines pass through the cut 304 to be concentrated on the second heating element 40, but where the first heating element 30 is located the electromagnetic inductive lines are concentrated on the first heating element 30. The second heating element 40 is installed on the base 10, when the tobacco cigarette 200 is received inside the chamber 201, the second heating element 40 is inserted into the tobacco cigarette 200 and generates a vertex to heat the tobacco cigarette 200, that means, heating the tobacco cigarette 200 inside directly thus to heat the tobacco cigarette 200 from inside to outside, with while the at least one first heating element 30 is heating the tobacco cigarette 200 from outside to inside, therefore the tobacco cigarette 200 is heated evenly. Moreover, since the first heating element 30 has a cut 304 for ensuring the second heating element 40 to absorb sufficient electromagnetic flux, such that improving the heating efficiency of the second heating element 40 heating the tobacco cigarette 200, further, making sure the tobacco cigarette 200 is heated evenly so a taste of the electronic cigarette 300 is improved.

Figure 7:
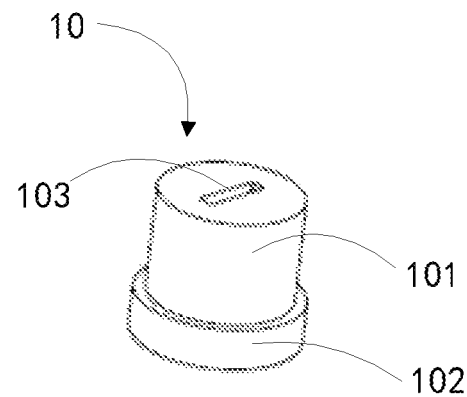
FIG. 7 is an isometric view of the base in the heating device.

With reference to FIG. 7, the base 10 includes a bulge part 101 and a substrate 102, the bulge part 101 is integral with the substrate 102. More specifically, the bulge part 101 and the substrate 102 are integral as a whole by casting or stamping technologies etc. no limitation herein. In some embodiments, the bulge part 101 may be detachably connected with the substrate 102. As used herein, the bulge part 101 is roughly a cylindrical structure; the bulge part 101 is inserted into the chamber 201 of the supporter 20 to install the supporter 20 on the base 10. The base 10 has a fastening structure 103 for fixing the second heating element 40 on the base 10. More specifically, the bulge part 101 has the fastening structure 103, and the fastening structure 103 is a groove, one end of the second heating element 40 is inserted into the groove, so the second heating element 40 is fixed on the base 10. In some embodiments, the second heating element 40 may be fixed on the base 10 via other methods, such as screw threads etc.

Referring to FIGS. 4 to 6, the supporter 20 is roughly a hollow cylinder, an inner diameter of the supporter 20 is roughly larger than an outer diameter of the bulge part 101, so the bulge part 101 is inserted into the supporter 20, and the supporter 20 is installed in the base 10. Since the supporter 20 is hollow, the supporter 20 has a chamber 201 therein for receiving the tobacco cigarette 200. More specifically, part of the tobacco cigarette 200 is received into the chamber 201, remaining part of the tobacco cigarette 200 protrudes outside the chamber 201.

Figure 8:
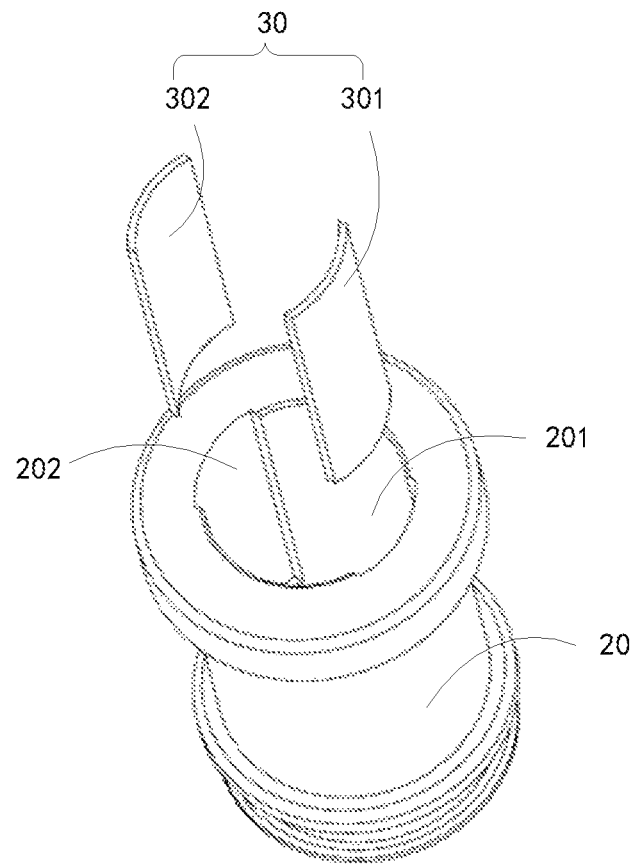
FIG. 8 illustrates connection between a supporter and a first heating element in the heating device in FIG. 4.

Referring FIG. 8, the at least one first heating element 30 is disposed in the chamber 201, more specifically, the inner wall of the supporter 20 has a slot 202 for engaging with the first heating element 30 that is installable on the base 20, so the at least one first heating element 30 is disposed in the chamber 201. When the tobacco cigarette 200 is received in the chamber 201, the at least one first heating element 30 is disposed between the tobacco cigarette 200 and the supporter 20, and the at least one first heating element 30 contacts the outer surface of the tobacco cigarette 200 and generates a vertex in the magnetic field to heat the tobacco cigarette 200, that means, the tobacco cigarette 200 is heated from outside to inside, which is the first direction as shown in FIG. 6. In the embodiments, the electromagnetic heating method is adopted to heat the tobacco cigarette 200, therefore, the at least one first heating element 30 is made by a metallic conductor, electromagnetic materials are preferred to bring a better effect of electromagnetic heating. In some embodiments, the at least one first heating element 30 is made of at least one or more selected from a group of iron powder, iron-nickel 50, sendust cores and MPP molypermalloy powder etc.

The at least one first heating element 30 has a cut 304 thereon extending along an axial direction of the electromagnetic induction coil 50. More specifically, the at least one first heating element 30 includes two first heating element, and two first heating elements are spaced from each other by a predetermined distance along a circumferential direction of an inner wall of the chamber, thus forming the cut 304. Since the electromagnetic induction coil 50 is provided in the embodiments of the present disclosure, the tobacco cigarette 200 is heated via the electromagnetic heating method. Therefore, to utilize the electromagnetic flux sufficiently and not to affect the second heating element 40 absorbing the electromagnetic flux, at least one first heating element 30 is needed to be wound around a periphery of the tobacco cigarette 200, forming the cut 304. For example, two first heating elements are disposed along the circumferential direction of the inner wall of the chamber 201, thus forming the cut 304, rather than a closed loop. As used herein, the number of the cuts 304 may be multiple, such as one, two, three or four etc. no limitation to the number of the cuts 304 herein.

More specifically, two first heating elements include a first arc-shaped heating piece 301 and a second arc-shaped heating piece 302 matched with the outer surface of the tobacco cigarette 200. The first arc-shaped heating piece 301 and a second arc-shaped heating piece 302 are disposed symmetrically at two sides of the second heating element 40, thus forming the cut 304 that ensures the second heating element 40 to absorb electromagnetic inductive lines for transformation, two first heating elements 30 symmetrically set at two sides of the second heating element 40 may make the tobacco cigarette 200 available for heating evenly.

In some embodiments, the two first heating elements may be integrated as a whole. More specifically, the two first heating elements may be a sleeve, the side wall of the sleeve is provided with two or more than two grooves extending along the axial direction of the sleeve, thus forming the cut 304.

Figure 9:
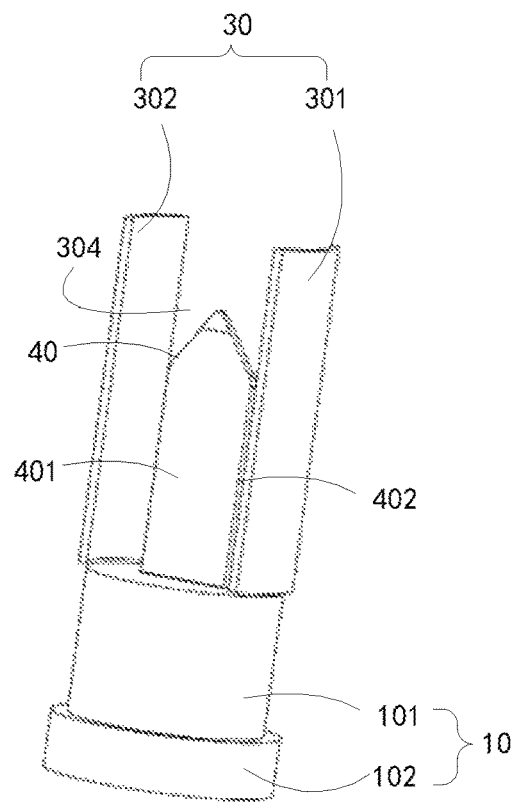
FIG. 9 illustrates connection between the base and a second heating element in the heating device in FIG. 4.
Figure 10:
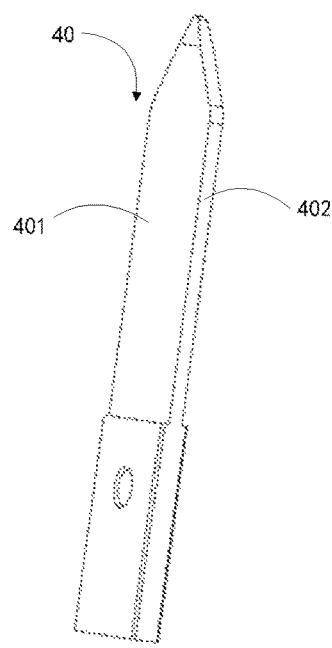
FIG. 10 illustrates the second heating element in the heating device in FIG. 4.

Referring to FIG. 9 and FIG. 10, the second heating element 40 is installed on the base 10; more specifically, one end of the second heating element 40 is inserted into the groove to fix the second heating element 40 on the base 10. When the tobacco cigarette 200 is received in the chamber 201, the second heating element 40 is inserted into the tobacco cigarette 200 and generates a vertex in the alternating magnetic field to heat the tobacco cigarette 200, therefore the tobacco cigarette 200 is heated from inside to outside, which is the second direction as shown in FIG. 6. The material of the second heating element 40 is similar with the at least one first heating element 30, that is the second heating element 40 is made by metallic conductor, permeability magnetic material is preferred which has better effect of electromagnetic inductive heating. For example, the second heating element 40 is made of at least one or more selected from a group of iron powder, iron-nickel 50, sendust cores and MPP molypermalloy powder etc.

The second heating element 40 is a laminated structure with a first surface 401 and a second surface 402. As used herein, an area of the first surface 401 is larger than that of the second surface 402, the first surface 401 faces the cut 304. More specifically, the first surface 401 is perpendicular with a line connecting with two ends of the second arc-shaped heating piece 302, and the second surface 402 is parallel with a line connecting with two ends of the first arc-shaped heating piece 301, and the second surface 402 is parallel with a line connecting with two ends of the second arc-shaped heating piece 302. Since the second heating element 40 is plate-shaped structure, the area of the first surface 401 is larger than that of the second surface 402, therefore, the second heating element 40 generates more heat on the first surface 401 than the second surface 402. Meanwhile, since between the first arc-shaped heating piece 301 and the second arc-shaped heating piece 302 has a cut 304, enabling temperature of the area near to the first arc-shaped heating piece 301 and the second arc-shaped heating piece 302 is higher than the temperature of the area near to the cut 304. By means of the first surface 401 perpendicular with the line connecting two ends of the first arc-shaped heating piece 301, and the first surface 401 perpendicular with the line connecting two ends of the second arc-shaped heating piece 302, the second surface 402 parallel with a line connecting two ends of the first arc-shaped heating piece 301, and the second surface 401 parallel with a line connecting two ends of the second arc-shaped heating piece 302, the tobacco cigarette 200 is further heated evenly, so as to improve the taste of the electronic smoking set 300.

Referring to FIGS. 4 to 6, the electromagnetic induction coil 50 is wound around the supporter 20; more specifically, the supporter 20 has a first position stop 205 and a second position stop 206. The electromagnetic induction coil 50 is wound around the supporter 20 between the first and second position stops 205, 206. The electromagnetic induction coil 50 is used to generate a changing magnetic field, such that the at least first heating element 30 and the second heating element 40 generate vortexes. More specifically, when an alternating current is passing through the electromagnetic induction coil 50, such as the fast changing high-frequency and high-voltage current passes through the electromagnetic induction coil 50, it would generate fast changing alternative magnetic field, the at least one first heating element 30 and the second heating element 40 are disposed in the alternative magnetic field to do cutting motion for cutting alternative magnetic field lines to generate alternating current, that is the vortex. The vortex makes carriers of the at least first heating element 50 and the second heating element 40 do high-speed and irregular motion, the carriers are crashing into one another and rubbing with one another to generate heat energy, so as to heat the tobacco cigarette 200. The electromagnetic induction coil 50 may be made by electricity conductive materials, such as, the electromagnetic induction coil 50 may be made by good electricity conductor with cheap price such as copper wires and aluminum filaments etc.

Understandable, in some embodiments, two electromagnetic induction coils 50 are provided, including a first coil (not shown) and a second coil (not shown), the first coil and the second coil are wound around a periphery of the supporter 20, and the number of the first coils and the second coils are different, so as to change heating speed of the at least first heating element 30 and the second heating element 40, therefore the heating effect is more flexible.

Understandable, in some embodiments, an outer surface of the electromagnetic induction coil 50 is coated with an insulating layer (not shown), the insulating layer is configured to avoid leakage of electricity through the electromagnetic induction coil 50. The insulating layer is made by insulating materials such as at least one or more selected from a group of synthetic resins, epoxy resins, phenolic resins, UP-4250, polyimide plastic, energy-concentrated resins and polyimide etc.

The heating device 100 further includes a heat insulating layer (not shown), the heat insulating layer is disposed between the electromagnetic induction coil 50 and the at least one first heating element 30, the heat insulating layer is configured for reducing heat in the chamber 20 transferring outside. The heat insulating layer is made by heat insulating materials, such as at least one or more selected from a group of heat insulation glue, aerogel, asbestos, aluminium silicate and calcium silicate etc. The heat insulating layer makes the heat not easy to loss, and is more safe to use, therefore improving heat efficiency and effect of heat preservation.

The heating device 100 further includes a temperature sensor 60, disposed on the second heating element 40. The temperature sensor 60 is used for temperature detecting. The temperature sensor 60 is used in a controller to send signals, the controller is used to control temperature of the heating device 100. As used herein, the controller is a controller allocated in the electronic cigarette 300, or a controller allocated in an exterior apparatus such as a terminal apparatus.

It needs to be illustrated, in some embodiments, the temperature sensor 60 may also be allocated on the at least one first heating element 30, or between the at least on first heating element 30 and the second heating element 40.

The power supply module 110 provided by the embodiments of the present disclosure is described hereinafter.

Figure 11:
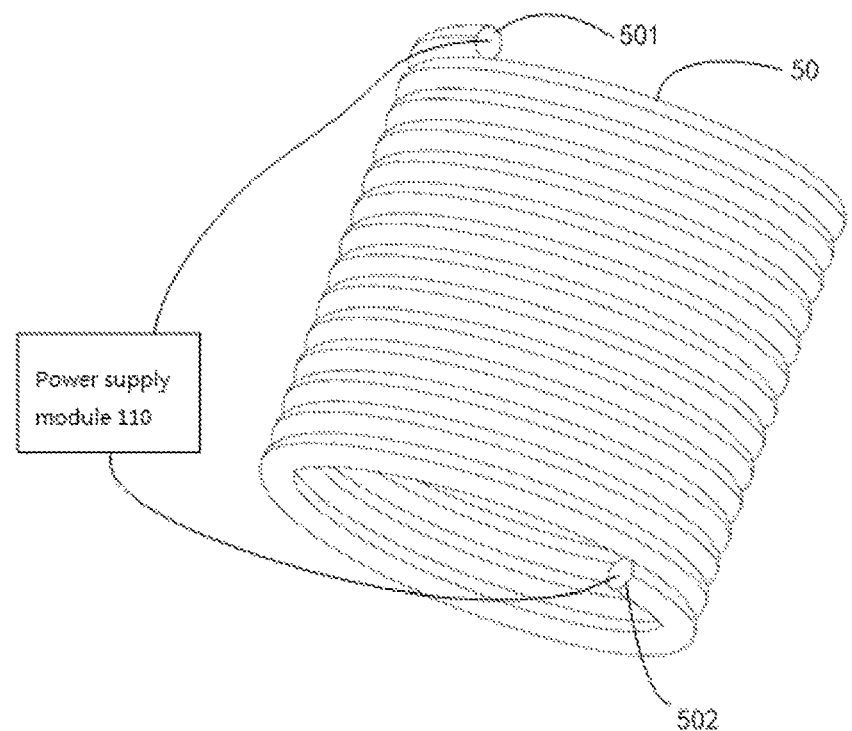
FIG. 11 illustrates connection between the electromagnetic inductive coil in FIG. 4 and the power supply module in FIG. 1.
Figure 12:
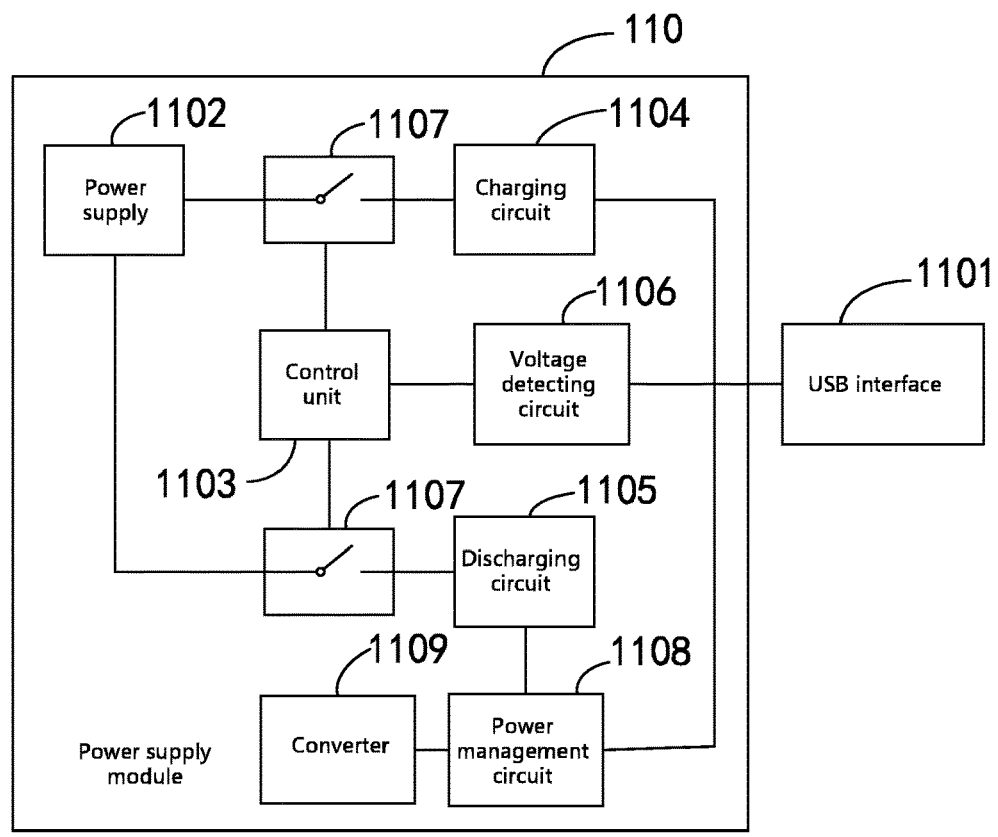
FIG. 12 is a block diagram illustrating the power supply module in the electronic smoking set in FIG. 1.

Referring to FIG. 11 and FIG. 12, the power supply module 110 is coupled with the electromagnetic induction coil 50 to supply an alternating current to the electromagnetic induction coil 50. Specifically, the electromagnetic induction coil 50 includes a first interface 501 and a second interface 502; the power supply module 110 may be coupled with the first interface 501 and the second interface 502, so as to be coupled with the electromagnetic induction coil 50. Thus the electromagnetic induction coil 50 generates electromagnetic induction. According to law of electromagnetic induction, when the power supply module 110 supplies the alternating current to the electromagnetic induction coil 50, the electromagnetic induction coil 50 generates alternating current so as to generate the alternative magnetic field. The at least one first heating element 30 and the second heating element 40 are disposed in the alternative magnetic field, doing cutting motion, that is, cutting alternative magnetic inductive lines to generate the alternating current, namely a vortex, therefore heating the tobacco cigarette 200.

As used herein, the power supply module 110 includes an USB interface 1101, a power supply 1102, a control unit 1103, a charging circuit 1104, a discharging circuit 1105, a voltage detecting circuit 1106, two switches 1107, a power management circuit 1108 and a converter 1109. The power supply 1102 is respectively coupled with the charging circuit 1104 and the discharging circuit 1105. Further, a switch 1107 is disposed between the power supply 1102 and the charging circuit 1104, and another switch 1107 is disposed between the power supply 1102 and the discharging circuit 1105. The charging circuit 1104 and the discharging circuit 1105 are both coupled with the USB interface 1101, coupled with the exterior power supply via an USB interface. The voltage detecting circuit 1106 is coupled with the USB interface 1101 to detect weather the power supply module 110 is coupled with the exterior power supply. The control unit 1103 is respectively coupled with two switches 1107 and the voltage detecting circuit 1106. The discharge circuit 1105 is coupled with the power management circuit 1108; the power management circuit 1108 is coupled with the converter 1109. The converter 1109 is configured for changing DC (direct current) to AC (alternating current), the converter 1109 is coupled with the electromagnetic induction coil 50 to supply power to it. If the voltage detecting circuit 1106 detects a voltage, that means the power supply module 110 is coupled with the exterior power supply, so the voltage detecting circuit 1106 sends signals to the control unit 1103 sends signals, the control unit 1103 receives that signal and controls the switch 1107 between the power supply 1102 and the charging circuit 1104, from "off" state is changed into "on" state, the current of the exterior power supply charges the power supply 1102. If the voltage detecting circuit 1106 fails to detect the voltage, the control unit 1103 receives that signal and controls the switch 1107 between the power supply 1102 and the discharging circuit 1105, that is, another switch 1107, from "off" state is changed into "on" state. The current of the power supply 1102 flows towards the convertor 1109 from the discharging circuit 1105 and the power management circuit 1108. The convertor 1109 changes DC to AC, thus supplying power to the electromagnetic induction coil 50.

In terms of the heating device 100 of the present disclosure, when the at least one first heating element 30 heats the tobacco cigarette 200 from outside to inside, while the second heating element 40 heats the tobacco cigarette 200 from inside to outside, therefore heating the tobacco cigarette 200 evenly. Moreover, since the at least one first heating element 30 has the cut 304 extending along the axial direction of the electromagnetic induction coil 50, which may ensure the second heating element 40 to absorb and transform sufficient magnetic flux, so as to improve the heating efficiency of the second heating element 40, consequently improving heating efficiency to the tobacco cigarette 200, further making the tobacco cigarette 200 heated evenly, making taste consistent and improving the taste of the electronic cigarette 300, eventually improving user experience.

Terminology used herein is for the purpose of describing particular embodiments only and is not intended to be limiting of the invention. Variations may be made to the embodiments and methods without departing from the spirit of the disclosure. Accordingly, it is appropriate that the appended claims be construed broadly and in a manner consistent with the scope of the disclosure.

What is claimed is:

1. A heating device for heating tobacco cigarette, comprising:
    a base;
    a supporter disposed on the base, the supporter comprising a chamber therein, the chamber being configured for receiving the tobacco cigarette;
    an electromagnetic induction coil wound around the supporter and configured for generating an alternative magnetic field in the chamber;
    at least one first heating element disposed in the chamber; when the tobacco cigarette is disposed in the chamber, the at least one first heating element contacts an outer surface of the tobacco cigarette and is configured for generating a vortex in the alternative magnetic field to heat the tobacco cigarette; and
    a second heating element disposed on the base; when the tobacco cigarette is disposed in the chamber, the second heating element is inserted into the tobacco cigarette and configured to generate a vortex in the alternative magnetic field to heat the tobacco cigarette;
    wherein, the at least one first heating element is disposed around a periphery of the second heating element, and the at least one first heating element forms a cut extending along an axial direction of the electromagnetic induction coil;
    wherein the at least one first heating element comprises two first heating elements; and the two first heating elements are spaced from each other by a predetermined distance along a circumferential direction of an inner wall of the chamber, thus forming the cut;
    wherein the second heating element is a plate-shaped structure with a first surface and a second surface; the first surface has a larger area than the second surface; the first surface faces the cut.

2. The heating device of claim 1, wherein the two first heating elements comprise a first arc-shaped heating piece and a second arc-shaped heating piece matched with the outer surface of the tobacco cigarette, and the first arc-shaped heating piece and the second arc-shaped heating piece are symmetrically disposed at two sides of the second heating element.

3. The heating device of claim 1, wherein the first surface is perpendicular with a line connecting two ends of the first arc-shaped heating piece; and the first surface is perpendicular with a line connecting two ends of the second arc-shaped heating piece; the second surface is parallel with a line connecting two ends of the first arc-shaped heating piece; and the second surface is parallel with a line connecting two ends of the second arc-shaped heating piece.

4. The heating device of claim 1, wherein the heating device further comprises a heat insulating layer; the heat insulating layer is disposed between the electromagnetic inductive coil and the at least one first heating element; the heat insulating layer is configured to reduce heat in the chamber transferring outside.

5. The heating device of claim 1, wherein the base comprises a bulge part and a substrate, the bulge part is inserted into the chamber of the supporter to allow the supporter to be installed in the base.

6. The heating device of claim 1, wherein the base comprises a fixing structure configured to fix the second heating element in the base.

7. The heating device of claim 1, wherein the heating device further comprises a temperature sensor, the temperature sensor is disposed on the second heating element or the at least one first heating element, or between the at least one first heating element and the second heating element.

8. A smoking set, comprising:
    a power supply module; and
    a heating device according to claim 1;
    wherein the power supply module is coupled with the electromagnetic inductive coil in the heating device and configured for supplying an alternating current to the electromagnetic inductive coil.

9. The smoking set according to claim 8,
    wherein the at least one first heating element comprises two first heating elements; and
    the two first heating elements are spaced from each other by a predetermined distance along a circumferential direction of an inner wall of the chamber, thus forming the cut.

10. The smoking set according to claim 9,
    wherein the two first heating elements comprise a first arc-shaped heating piece and a second arc-shaped heating piece matched with the outer surface of the tobacco cigarette, and the first arc-shaped heating piece and the second arc-shaped heating piece are symmetrically disposed at two sides of the second heating element.

11. The smoking set according to claim 10,
    wherein the second heating element is a plate-shaped structure with a first surface and a second surface; the first surface has a larger area than the second surface; the first surface faces the cut.

12. The smoking set according to claim 11,
    wherein the first surface is perpendicular with a line connecting two ends of the first arc-shaped heating piece; and the first surface is perpendicular with a line connecting two ends of the second arc-shaped heating piece; the second surface is parallel with a line connecting two ends of the first arc-shaped heating piece; and the second surface is parallel with a line connecting two ends of the second arc-shaped heating piece.

13. The smoking set according to claim 8,
    wherein the heating device further comprises a heat insulating layer; the heat insulating layer is disposed between the electromagnetic inductive coil and the at least one first heating element; the heat insulating layer is configured to reduce heat in the chamber transferring outside.

14. The smoking set according to claim 8,
    wherein the base comprises a bulge part and a substrate, the bulge part is inserted into the chamber of the supporter to allow the supporter to be installed in the base.

15. The smoking set according to claim 8, wherein the base comprises a fixing structure configured to fix the second heating element in the base.

16. The smoking set according to claim 8, wherein the heating device further comprises a temperature sensor, the temperature sensor is disposed on the second heating element or the at least one first heating element, or between the at least one first heating element and the second heating element.

\* \* \* \* \*